United States Patent [19]
Ray

[11] Patent Number: 5,125,396
[45] Date of Patent: Jun. 30, 1992

[54] SURGICAL RETRACTOR

[76] Inventor: R. Charles Ray, 1515 S. "K" St., Tacoma, Wash. 98405

[21] Appl. No.: 593,195

[22] Filed: Oct. 5, 1990

[51] Int. Cl.⁵ ............................................. A61B 17/02
[52] U.S. Cl. ..................................... 128/20; 606/198
[58] Field of Search .............................. 128/3, 17–20, 128/207.29; 604/104–109; 606/90, 167, 180, 197, 198, 199

[56] References Cited

U.S. PATENT DOCUMENTS

| | | | |
|---|---|---|---|
| 328,619 | 10/1885 | Sperry | 128/17 |
| 1,493,240 | 5/1924 | Bohn | 606/180 |
| 2,083,573 | 6/1937 | Morgan | 606/198 |
| 3,312,222 | 4/1967 | Dwyer | 606/198 |
| 3,788,318 | 1/1974 | Kim et al. | 606/198 |
| 3,789,852 | 2/1974 | Kim et al. | 606/198 |
| 4,130,113 | 12/1978 | Graham | 128/20 |

FOREIGN PATENT DOCUMENTS 459218 11/1976 U.S.S.R. ............................ 606/198

Primary Examiner—Stephen C. Pellegrino
Assistant Examiner—Ralph A. Lewis
Attorney, Agent, or Firm—Christensen, O'Connor, Johnson & Kindness

[57] ABSTRACT

A surgical retractor of the type used to retract tissue or muscles during a surgical operation. A retractor (20) comprises an outer ring (24) having a downwardly extending outer arcuate blade (24a) and an inner ring (22) having a downwardly extending inner arcuate blade (22a). The inner ring is nested within the outer ring such that the inner arcuate blade is rotatable from a first position overlapped to the outer arcuate blade, to a second position in which it is diametrically opposite the outer blade. A first handle (26) is used to hold the outer ring while a second handle (28) rotates the inner ring. The surgical retractor is inserted into an incision with the arcuate blades in the first position and the outer and inner rings are rotated to spread muscle and tissue.

8 Claims, 3 Drawing Sheets

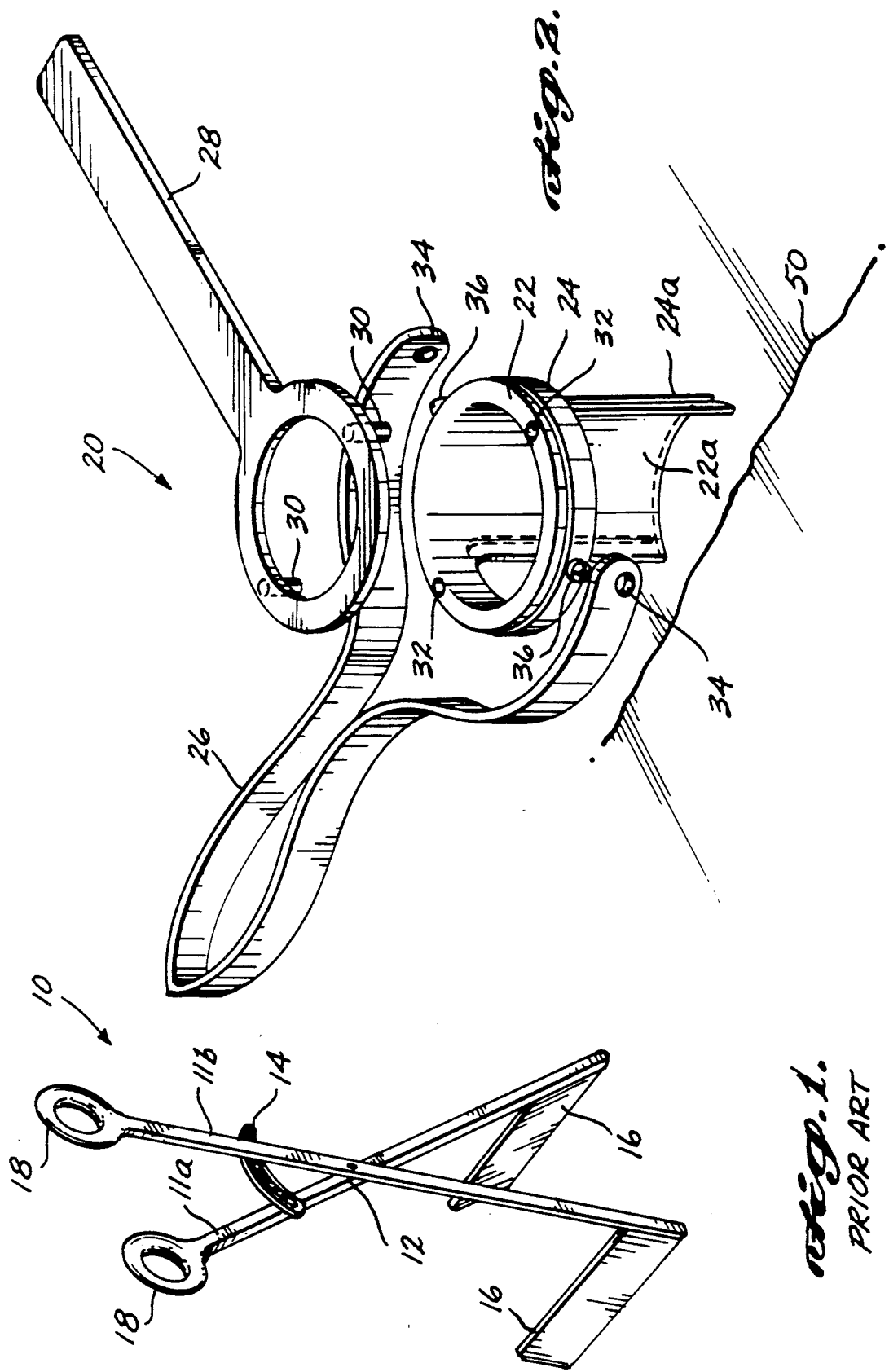

SURGICAL RETRACTOR

FIELD OF THE INVENTION

The invention relates generally to medical retractors, and more specifically, to retractors used to separate tissues or muscles to aid visualization in order to perform a surgical procedure.

DESCRIPTION OF THE PRIOR ART

In certain types of surgical procedures, such as when performing surgery on the spine, it is often necessary to retract connective tissue or muscle in order to provide the surgeon clear access to and visibility of the area of the pathology. A special surgical retractor is usually employed to spread apart or retract tissue or muscle in the surgical field. Although numerous types of surgical retractors are in use, FIG. 1 illustrates a retractor 10, which is generally exemplary of prior art devices of this type.

Retractor 10 comprises two levers 11a and 11b that are pivotally connected in a scissor-like configuration 12. At one end of each lever 11a and 11b are disposed blades 16, and finger loops 18 are provided at the opposite ends of the levers. An arcuate arm 14 extends from one side of lever 11a, and includes a ratchet surface that engages lever 11b to hold the blades 16 of the retractor apart.

The problem with surgical retractors of the type shown in FIG. 1 is that blades 16 and levers 11a and 11b often are not strong enough to spread or retract muscle and connective tissue without bending, particularly when the surgeon is operating on the spine. Before a surgeon can perform any operation on the spine the paraspinal muscles must be retracted. Due to the strength of the muscles and the muscles that surround the spine, prior art retractor 10 is inadequate to perform this type of surgery. Merely increasing the thickness or cross section of the levers and blades of retractor 10 is not an acceptable solution, since the retractor cannot be so massive that it interferes with the surgical procedure.

SUMMARY OF THE INVENTION

In accordance with the present invention, a surgical retractor for use in retracting tissue during a medical procedure comprises a first ring having a downwardly extending outer arcuate blade and a second ring having a downwardly extending inner arcuate blade. The first and second rings are rotatably connected to each. As a result, the inner and outer arcuate blades are rotatable in respect to each other from a first position in which the inner and outer blades are substantially overlapped to a second position in which the inner and outer blades are substantially diametrically opposed. Thus, by rotating the first and second rings relative to each other, the surgeon can spread tissue, thereby creating a space between the inner and outer arcuate blades in which to operate.

BRIEF DESCRIPTION OF THE DRAWINGS

FIG. 1 is generally illustrative of retractors found in the prior art.

FIG. 2 is an isometric exploded view of a retractor according to the present invention.

DESCRIPTION OF THE PREFERRED EMBODIMENT

Figure 5:
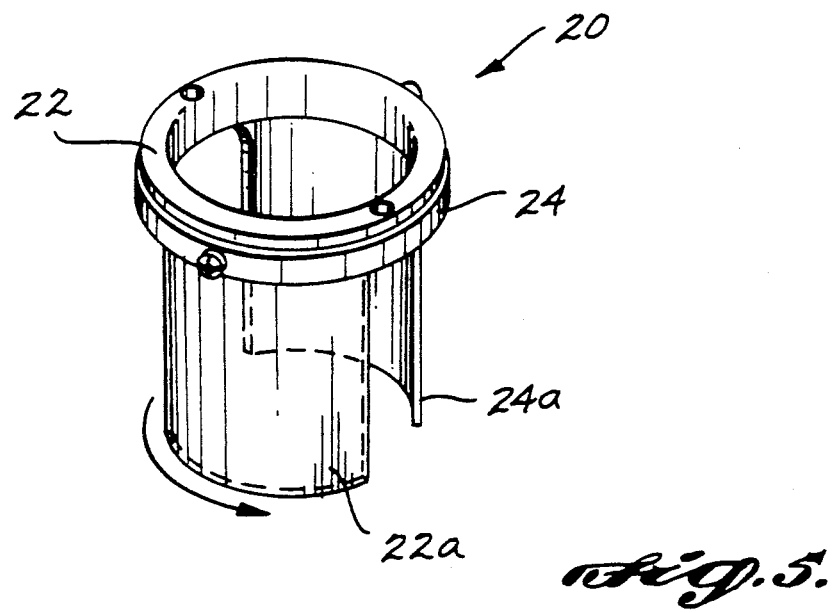
FIG. 5 is an isometric view showing the retractor as it appears when rotated to separate tissue.

A surgical retractor 20 that is capable of retracting muscle and strong connective tissue is shown in FIG. 2. The retractor 20 comprises an inner ring 22 having a downwardly extending arcuate blade 22a nested within an outer ring 24, which has a downwardly extending arcuate blade 24a. The inner ring 22 is concentrically rotatable with respect to the outer ring 24. A first handle 26 is removably attached to outer ring 24 and is used to secure the position of the outer ring 24 while a second handle 28 rotates the inner ring 22. The outer ring 24 has a pair of set screws 36 that engage holes 34 in the first handle 26 and secure the inner ring 22 within the outer ring 24. The second handle 28 includes pins 30 that are positioned to engage holes 32 found on the inner ring 22. When thus connected to the inner ring 22, the second handle is used to rotate it with respect to the outer ring 24.

Figure 3:
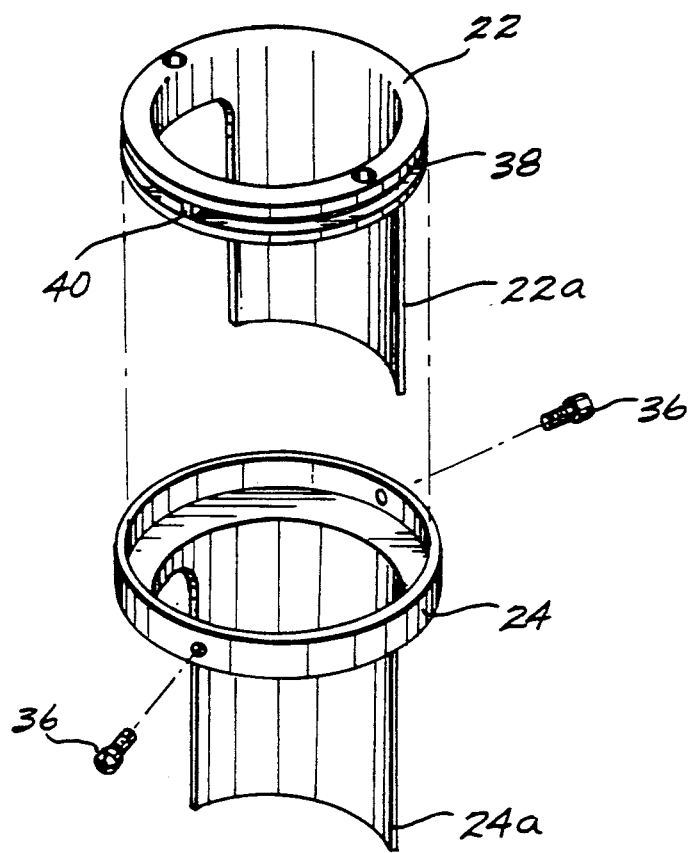
FIG. 3 is an exploded view of an inner ring and an outer ring that comprise the retractor.

FIG. 3 shows further details of the retractor 20. The inner ring 22 nests within the outer ring 24 and is rotatably secured thereby the two set screws 36. The inner ring 22 contains an annular groove 38 (also shown in FIG. 4) in which the ends of set screws 36 extend, allowing the inner ring 22 to rotate while maintaining the nested configuration of the rings. The inner ring 22 also contains a stop 40 that is positioned within the groove 38 in order to limit the rotation of the inner ring 22 to approximately 180° with respect to the outer ring 24.

Figure 4:
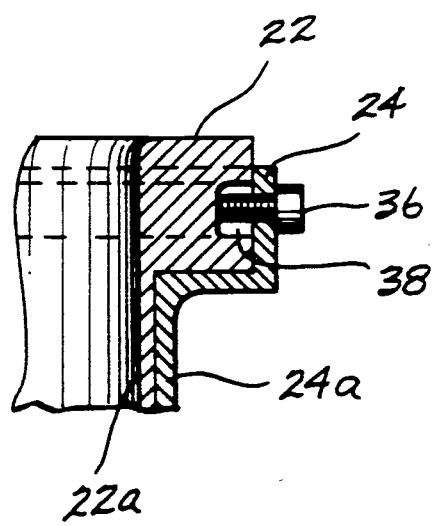
FIG. 4 is a cross-sectional view of a portion of the inner and outer rings showing how the inner ring is secured to the outer ring.

FIG. 4 shows clearly how the inner ring 22 is rotatably secured to the outer ring 24. The set screws 36 engage the groove 38 in the inner ring 22, thereby securing the inner ring 22 to the outer ring 24, yet still allow for rotation of the inner ring 22.

FIG. 5 illustrates the disposition of the inner ring 22 after it is rotated with respect to the outer ring 24 to separate tissue. The retractor 20 is first placed into an incision 50 (shown in FIG. 1) and then the inner ring 22 is rotated with respect to the outer ring 24 in order to spread the tissue to each side of the incision, creating a space between the arcuate blades 22a and 24a in which a surgeon can operate.

The surgical retractor of the present invention can be formed or machined from a surgical grade stainless steel according to methods well known in the art. In the preferred embodiment, arcuate blades 22a and 24a extend in an arc approximately 40° to 60° around the inner ring 22 and outer ring 24, respectively. However, it is recognized that other sizes of the arcuate blades 22a and 24a could be used without impairing the operation of the retractor. Retractor 20 thus provides a simple and effective surgical retractor having blades of greater strength, due to their arcuate shape, than prior art retractors and can be used in surgical procedures requiring the separation of strong connective tissue or muscle groups without fear that the blades will deform.

Although the present invention has been described with reference to the preferred embodiment, workers skilled n the art will recognize that changes may be made in form and detail without departing from the spirit and scope of the invention.

The embodiments of the invention in which an exclusive property or privilege is claimed are defined as follows:

1. A surgical retractor for use in retracting tissue during a medical procedure comprising:
   a first ring means having attached thereto a downwardly extending outer arcuate blade disposed adjacent the perimeter of the first ring; and
   a second ring means having attached thereto a downwardly extending inner arcuate blade disposed adjacent the perimeter of the second ring, the first and second ring means being rotatably connected to each other such that the inner and outer arcuate blades are rotatable with respect to each other from a first position in which the inner and outer arcuate blades are substantially overlapped to a second position in which the inner and outer arcuate blades are substantially diametrically opposed, said first and second ring means cooperating to define an aperture through which a surgeon can operate when said inner and outer arcuate blades are rotated to the second position.

2. The surgical retractor as defined by claim 1 further comprising:
   a first handle attached to the first ring; and
   a second handle attached to the second ring.

3. The surgical retractor as defined in claim 2, wherein:
   the first handle and second handle provide leverage to rotate the inner and outer arcuate blades from the first position to the second position.

4. The surgical retractor as defined in claim 2, further comprising:
   connection means for allowing easy connection and removal of the first and second handle to the first and second rings.

5. The surgical retractor as defined in claim 1 further comprising:
   means for limiting the rotation of the first ring with respect to the second ring as the inner and outer arcuate blades are rotated to their second position.

6. The surgical retractor as defined in claim 1, wherein the second ring further comprises an annular grove, and the first ring includes a set screw that engages the annular groove to rotatably connect the first ring to the second ring.

7. The surgical retractor as defined in claim 1, wherein the inner and outer arcuate blades extend in an arc of between 40° and 60° around the first and second rings, respectively.

8. A surgical retractor for use in retracting tissue during a medical procedure comprising:
   a first arcuate blade;
   a second arcuate blade nested within said first arcuate blade; and
   means for mounting said first and second arcuate blades such that they are rotatable about a substantially common axis from a first position in which the first and second arcuate blades are substantially overlapped to second position in which the first and second blades are substantially diametrically opposed relative to said axis, said means for mounting defining an aperture through which a surgeon can operate that is located between said blades when the first and second arcuate blades are rotated to the second position.

* * * * *

UNITED STATES PATENT AND TRADEMARK OFFICE
CERTIFICATE OF CORRECTION

PATENT NO. : 5,125,396

DATED : June 30, 1992

INVENTOR(S) : R. Charles Ray

It is certified that error appears in the above-identified patent and that said Letters Patent is hereby corrected as shown below:

TITLE PAGE:

[56] References Cited      Please add the following U.S. patent documents:

2,812,758 11/1957 Blumenschein (Class 128/Subclass 20)
    3,030,947 04/1962 Engelbert (Class 128/Subclass 3)
    3,750,652 08/1973 Sherwin (Class 128/Subclass 17)
    3,766,910 10/1973 Lake (Class 128/Subclass 20)
    4,502,485 03/1985 Burgin (Class 128/Subclass 321)
    4,747,395 05/1988 Brief (Class 128/Subclass 20)
    4,765,311 08/1988 Kulik et al. (Class 128/Subclass 3)

Signed and Sealed this

Seventh Day of September, 1993

*Attest:*

BRUCE LEHMAN

*Attesting Officer*      *Commissioner of Patents and Trademarks*